United States Patent [19]

Herstein

[11] Patent Number: 5,616,332
[45] Date of Patent: Apr. 1, 1997

[54] COSMETIC SKIN-RENEWAL-STIMULATING COMPOSITION WITH LONG-TERM IRRITATION CONTROL

[76] Inventor: Morris Herstein, P.O. Box 209, Scarsdale, N.Y. 10583

[21] Appl. No.: 410,387

[22] Filed: Mar. 27, 1995

Related U.S. Application Data

[63] Continuation of Ser. No. 97,380, Jul. 23, 1993, abandoned.
[51] Int. Cl.$^6$ ................. A61K 7/00; A61K 7/48
[52] U.S. Cl. ................. 424/401; 514/847; 514/859
[58] Field of Search ................. 424/401; 514/847, 514/859

[56] References Cited

U.S. PATENT DOCUMENTS

| | | | |
|---|---|---|---|
| 4,105,783 | 8/1978 | Yu | 424/283 |
| 5,002,760 | 3/1991 | Katzer | 514/847 |
| 5,190,876 | 3/1993 | Merrill | 435/240.2 |
| 5,238,965 | 8/1993 | Piazza | 514/847 |
| 5,252,604 | 10/1993 | Nagy | 514/859 |

OTHER PUBLICATIONS

Aged Skin, Retinoids, and Alpha Hydroxy Acids by Raoul Hermitte, PhD; "Cosmetics & Toiletries" vol. 107, Jul. 1992 pp. 63–64, 66–67.

*Primary Examiner*—Sallie M. Gardner
*Attorney, Agent, or Firm*—Handal & Morofsky

[57] ABSTRACT

A cosmetic skin-renewal stimulating composition suitable for daily use by consumers and providing anti-aging benefits with control of delayed irritation. The invention adds small quantities of a naturally occurring small-molecule, biologically active, aliphatic aminodiol lipid, for example sphingosine, to cosmetics incorporating a skin-renewal stimulating acid, for example lactic, hydroxybenzoic or retinoic acid, to provide control of deferred hyperproliferative allergenicity induced by the skin-renewal stimulating acid. Comparative data show a beneficial control of long-term irritation induced by several weeks of daily use of a variety of skin-renewal stimulating acids. The novel activity is displayed by sphingosine alone among several classes of biologically active skin lipids, in a selective and surprising manner. The results suggest applicability of the invention to wider classes of cell-proliferation agents for the control of deferred hyperproliferative allergenicity.

4 Claims, No Drawings

COSMETIC SKIN-RENEWAL-STIMULATING COMPOSITION WITH LONG-TERM IRRITATION CONTROL

This application is a continuation of application Ser. No. 08/097,380, filed July 23, 1993, now abandoned.

TECHNICAL FIELD

This invention relates to a novel skin-renewal stimulating composition and its method of application or use. More particularly, it relates to a cosmetic composition, especially a cosmetic composition suitable for daily use, which can improve the appearance and condition of the skin by stimulating, or increasing the rate of, cell renewal. Some such compositions are known as exfoliants and, more potent exfoliants are known as skin peels. Skin peels are usually applied under professional supervision. Often one application, accompanied by suitable preparatory treatments such as degreasing and abrasion, is adequate to induce peeling and promote the growth of a "new" skin.

BACKGROUND

It is well known, and the subject of ordinary biology text books, that the skin is a complex system with protective epidermal layers, growing endodermal layers, often a keratinous outer layer, systems of glands and follicles and systems for the supply of intracellular and extracellular fluids. Active methods and compositions for treating the skin which do more than provide a passive coating on it, must take account of its complexity.

Skin renewal can be stimulated, as a natural process, by removal of the outer keratinous layer of the skin system. Such removal can be effected mechanically, for example, abrasively by rubs, brushing and even scraping, or shaving. Chemical exfoliation and peeling are effected by agents that interact with the complex structure of the skin.

Known skin-renewal stimulating compositions and agents can provide anti-aging benefits, for example, a reduction of effects such as keratoses, freckles, wrinkles, elastosis and epidermal and dermal atrophy.

Recent years have seen the widespread use, by consumers and professionals alike, of a range of cosmetic and pharmacological formulations providing anti-aging and dermatologically therapeutic benefits. Active ingredients of these formulations typically include an alpha hydroxy acid ("AHA's" in the popular literature) or a retinoic acid ( marketed under the names RETINA or RENOVA, trademarks of Ortho Pharmaceuticals). Some currently available commercial formulations are described in "Mirabella", January 1993, pages 60–61.

Reputable scientific and clinical reports, as well as much subjective evidence have shown that substantial improvements in skin appearance and condition can be obtained by means of skin-renewal stimulating acids. In general terms, these improvements are believed to be attributable to increased rates of skin cell renewal, and the removal of outer layers of dead cells.

It is also well known that skin-renewal stimulating acids can be irritating, and that the irritation they induce is often a long-term effect manifested several weeks after use of the acids. In extreme cases the irritation can be severe, damaging and painful. Hermitte et al. "Aged Skin, Retinoids and Alpha Hydroxy Acids" Cosmetics and Toiletries 107 pp. 63–67 (July 1992) provides a short review of the title subject, with a substantial bibliography of forty references. The disclosures of Hermitte et al. and the references listed therein are herein incorporated by reference thereto. Such disclosure includes details of many skin-renewal stimulating acids that can be used in the practice of the present invention.

SUMMARY OF THE INVENTION

The invention, as claimed, is intended to provide a remedy. It solves the problem of reducing long-term irritation induced by topical application of skin-renewal stimulating acids to the skin. The invention solves this problem by formulating the acids, either as a cosmetic or a medication, with a small quantity of a sphingosine material. Sphingosine is one of a vast number of naturally occurring lipids or fatty substances that is present in the skin of mammals and is believed safe as well as effective and substantially free of side effects.

Clinical studies we have conducted have shown a surprising and selective activity of sphingosine in controlling long-term irritation produced by repeated applications of small dosages of skin-renewal stimulating acids. Our test results show that, other classes of skin lipids, namely phospholipids, cerobrosides and ceramides, show little if any activity, in controlling long-term irritation. Of the materials tested, sphingosine alone displayed a clear reduction of a pronounced irritation that was induced in volunteers by four weeks of treatment with topically applied doses of skin cell-renewal stimulating acids, namely, alpha hydroxy acids and tretinoin, an isomer of retinoic acid. Ceramides, in particular, which have recently been used in combination with alpha hydroxy acids in moisturizing products, showed no significant activity, in clinical studies, in reducing either immediate or long-term irritation.

Accordingly, the novel cosmetic and medicant compositions of my invention are expected to provide new, consumer and over-the-counter products that offer the effectiveness of known skin-renewal stimulating acids without the unpleasant, and sometimes damaging, long-term irritation wit which the use of these acids has heretofore been associated.

Further data we have obtained indicates that the role of an added sphingosine material in controlling long-term irritation, induced by skin-renewal stimulating acids, may be attributable to a more general role of replacing deficiencies of sphingosine caused by cellular immaturity. In keeping with these findings, the invention also provides a cell-renewal stimulating composition for topical application generally to epithelial tissue. In this aspect of the invention, enough sphingosine material to compensate for sphingosine deficiencies attributable to cellular immaturity is incorporated in a composition designed to stimulate increased cell proliferation by incorporation of a suitable, known stimulatory agent, such as a drug or a hormone.

BEST MODE FOR CARRYING OUT THE INVENTION

In searching for a material to control long-term irritation, one avenue of inquiry is to investigate the substances that are found occurring naturally in the skin.

Rieger "Skin Constituents as Cosmetic Ingredients" Cosmetics and Toiletries 107 85–94 (November 1992) reviews the state of the art of skin constituents from the point of view of their suitability and efficacy as cosmetic ingredients. Of the myriad skin constituents, a large class is comprised by lipid, or hydrophobic, fatty or fat-related materials.

Described by Rieger as bewilderingly complex, (last two lines of the left-hand column of page 87), the composition of sebaceous lipids, one source of the lipid materials in the intercellular spaces of the epidermis, includes squalene, sterols, wax and sterol esters and triglycerides. Another source of lipid materials is provided by production of sphingosine in basal keratinocytes, from which a wide class of sphingolipid materials is enzymatically synthesized. Acylation of sphingosine, phytosphinganine, or derivatives of either, produces ceramides. Glycosation of ceramides yields cerebrosides. Ceramides and cerebrosides are additional classes of lipids found in the skin. In addition to sphingolipids and sebaceous lipids, other substances, like cholesterols, alkanes and free fatty acids, are also present. Phospholipids are reported by Rieger as not being present in the stratum corneum, or outer layer of the skin though they are important lipid constituents of basal skin layers.

Jass et al. "The Living Stratum Corneum: Implications for Cosmetic Formulation", Cosmetics and Toiletries" 106 47–53 (October 1991), citing an earlier reference, report concentrations of lipids found variously in the inner basal and spinous layers of the epidermis, in the granular layer and in the outer stratum corneum. Sphingolipids are remarkable for showing an increase in concentration, proceeding outwardly through these layers, from about 7.3% of the (presumably intercellular) total lipid content of the basal layer to about 24.4% in the stratum corneum where their presence is believed important to the skin's barrier function and to prevention of loss of water vapor. By the time they reach the outer, stratum corneum, it appears from the reported data that glycolipids (cerebrosides) are, like phospholipids, substantially degraded, in this case to ceramides. The fate of sphingosine, which is not properly described as a sphingolipid, is not reported and it is not clear whether Jass et al.'s studies included sphingosine determinations.

In contrast to sphingolipids, phospholipids decline dramatically from about 44.5% in the basal layers to about 6.6% in the stratum corneum.

Clearly, no feasible research project could study all skin constituents, or even all lipid constituents. The field of study has to be narrowed down.

Rieger offers some principles for evaluating skin constituents for cosmetic use, including guidelines as to groups of substances not likely to be active in cosmetic formulations. The stratum corneum, or outer layer of the skin is not generally permeable to large molecules. Accordingly, molecules over about 4–5,000 molecular weight are contraindicated for cosmetic uses that depend upon permeation through the stratum corneum (last complete paragraph, right-hand column page 86) for their activity Phospholipids are contra-indicated by the probability of hydrolytic attack and degradation, as they find their way through the epidermis to keratinocytes. With regard to sphingolipids, Rieger concluded that there is no evidence that cosmetically supplied components of ceramides, (except for linoleic acid) can be properly incorporated in the stratum corneum (last paragraph, right-hand column of page 88). This conclusion does not suggest that ceramide components would be useful as active cosmetic ingredients. In contrast, Petersen in "Ceramides: Key Components for Skin Protection", Cosmetics and Toiletries 107 pp 45–49 (February 1992) concludes that, from a pharmaceutical and cosmetic point of view, ceramides are among the most important compounds for skin protection.

With regard to sphingosine, (a structural component of ceramides), Rieger notes that although sphingosine occupies a key role in the structure of many lipids, glycosphingolipids (cerebrosides), seem to exert structure-specific effects on the in vitro proliferation rates of human keratinocytes. This would suggest that cerebrosides rather than sphingosine would be useful in stimulating skin cell renewal. Current literature reports known to applicants lack clear teachings as to the presence or function, if present, of sphingosine in significant quantities in the stratum corneum.

Many in vitro, and small-mammal investigations of the mechanism of action of sphingosine have been conducted, from which sphingosine has become known as a protein kinase inhibitor, leading to suggestions that it may be useful in the treatment of diseases, or clinical disorders, such as psoriasis. One such report is from Gupta et al. "Sphingosine Inhibits Phorbol Ester Induced Inflammation etc." J. Invest. Dermatol. 91: 486–491, 1988. The data relates to mouse skin so that any conclusions that may be drawn from it carry uncertainty as to whether they accurately model the behavior of human skin.

Neither Gupta et al., nor any other art, suggests that sphingosine can control long-term irritation induced by skin-renewal stimulating acids, or suggests that sphingosine can improve the long-term performance of skin-renewal stimulating acids. Control of immediately induced contact irritation is not an appropriate indicator of an ability to control long-term irritation, as the data reported herein will show. Long-term irritation is induced by a different mechanism from short-term.

In the light of the foregoing knowledge of the art, we initiated clinical studies designed to evaluate, for their efficacy in controlling undesirable long-term side effects of skin-renewal stimulating acids, a practical range of skin lipid materials. For this purpose, we selected a limited number of groups of lipid substances, namely sphingosine, ceramides, cerebrosides and a representative phospholipid, lecithin. This line of investigation was pursued in spite of the cost of some of these materials which presents a formidable barrier to their use in cosmetic preparations, for example, the cost of one source of sphingosine is of the order of $5,000.00 per kilogram, for a twenty percent material, and that of ceramides and cerebrosides is comparable.

As will be reported and explained hereinbelow, the data we obtained showed sphingosine to have a surprising activity not shared by cerebrosides or ceramides, or by the tested phospholipid.

Broadly stated, the present invention provides a skin-renewal-stimulating, cosmetic composition for frequent and repeated, or daily, topical application to normal skin. The composition has an acidic pH and comprises a cosmetically acceptable, skin-cell-renewal stimulating acid or acids, present at a sufficient concentration to improve the appearance of the skin, together with a proportion of a sphingosine material sufficient to control long-term irritation.

Sphingosine Material

The preferred sphingosine material for use in practicing this invention is sphingosine itself, in a substantially pure form, so far as availability permits. Sphingosine is characterized under that name and monograph number 8703 in The Merck Index (Merck & Co. Inc.) eleventh edition 1989. It is a chiral, amino diol with a thirteen-carbon aliphatic chain substituent, constituting a hydrophobic tail having a structural formula which may be depicted as follows:

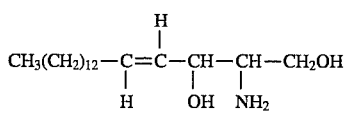

Preferably the naturally occurring D(+)-erythro enantiomer is used. To this end, sphingosine derived from biological sources, for example bovine brain extracts, can be used, although currently active research efforts suggest that synthetic sphingosine enantiomers, or racemic mixtures, may soon become available.

Those skilled in the art will be familiar with equivalent compounds to sphingosine itself, that display comparable activity to sphingosine, and can be used in practicing the present invention. Such compounds include analogs, homologs, enantiomers and derivatives not only of sphingosine but also of phytosphinganine, and dihydrosphingosine (sphinganie. Some such compounds, and their syntheses, are described in U.S. Pat. No. 5,110,987 (Liotta eta al.), U.S. Pat. No. 4,952,683 (Tschannen et al.) and U.S. Pat. No. 4,937,328 (Schmidt et al.), the disclosures of which are herein incorporated by reference thereto.

Such sphingosine equivalents should, until a precise mechanism of action of sphingosine in achieving the surprising results of the present invention is clearly known, apparently, preferably include the main chemical features of sphingosine, namely an electropositive nitrogen atom near one or two electronegative oxygen atoms, preferably juxtaposed in one region of the molecule with a double bond providing a center of optical activity, and a hydrophobic tail. Preferably also, at least one hydroxyl and the amino group are either available as such, or freely available for substitution.

More preferred sphingosine equivalents retain, or will liberate, both hydroxyls, the amino group and the double bond.

Skin-renewal Stimulating Acids

In general terms the skin-renewal stimulating acid can be a hydrophilic acid or other acid-equivalent electronegatively hydrophilic organic compound selected from the group consisting of hydroxycarboxylic acids, keto acids, keto esters, hydroxybenzoic acids and related compounds. Preferred compounds are relatively lower molecular weight as higher molecular weight compounds tend to be hydrophobic and may have too little activity. Since the smallest molecules such as formic acid, are unduly aggressive and not readily subject to control, a preferred molecular weight range is from about 50 to about 250.

Moreover, relevant biological activity appears to require for the simpler, non-receptor binding acids, which lack the hormone-like activity attributable to receptor binding of the retinoids, close proximity between the hydroxyl or keto groups and the carboxyl group. Preferably they should be substituents of one and the same carbon atom.

In one group of preferred embodiments, the skin-cell-renewal stimulating acid is a hydrophilic acid selected from the group consisting of alpha hydroxy carboxylic acids, alpha keto carboxylic acids and hydroxybenzoic acids.

Preferably, the acid, or acid equivalent, is selected from the group consisting of glycolic acid, lactic acid, malic acid, tartaric acid, citric acid, ascorbic acid, mandelic acid, azelaic acid, glyceric acid, tartronic acid, gluconic acid, benzilic acid, pyruvic acid, ethyl pyruvate, 2-hydroxybutyric acid, and mixtures thereof. Although mineral acids in appropriate concentrations, may stimulate skin cell renewal, they are not believed to be susceptible to irritation control by the present invention, nor are highly polar non-hydroxy acids, for example trichloracetic acid. Ascorbic acid is a special case of a hydroxy acid which has some application in skin-renewal stimulation, but is not generally suitable for incorporation in cosmetic skin-renewal stimulating formulations as it tends to brown in such formulations at active concentrations of about 5 to 10 weight-for-weight. Ascorbic acid, in lower concentrations, has important applicability as an antioxidant, in the practice of this invention, as will be described hereinbelow.

Preferably, the alpha hydroxy acid used in the inventive compositions is a straight or branched chain aliphatic acid with not more than three substituents in the aliphatic backbone, the substituents being non-basic and being selected from the group consisting of hydroxy, aldehyde, keto, carboxyl, chloro and nitro.

In another group of preferred embodiments, the skin-cell-renewal stimulating acid is a hydrophobic acidic retinoid, for example tretinoin, or retinoic acid.

Various skin-renewal stimulating acids may be combined together, and simple tests can be used to evaluate the efficacy and side effects of skin renewal acids, for incorporation into cosmetics suitable for daily application to the skin, hair or nails.

The invention is also applicable to, and can use other skin-renewal stimulating acids such as those described in the literature cited above. Preferred are acids with good, cosmetically acceptable characteristics, especially freedom from any unpleasant odor, low or substantially no toxicity, stability for shelf life, freedom from regulatory problems, known and tolerable side effects and a white or colorless, appearance in end product compositions, as well as the ability to be easily formulated in traditional cosmetic compositions. Sphingosine and equivalents preferably also meet these requirements.

Relative proportions of ingredients

An effective amount of sphingosine can be found in the range of from about 0.001 to 5% by weight of a topically applied skin treatment composition, preferably, about 0.005 to about 0.2%. Strong activity is shown at concentrations of about 0.01 to 0.1%. Because of the presently high cost of sphingosine, the lowest effective concentrations are preferred.

A suitable concentration of hydrophilic skin-renewal stimulating acid, in cosmetics intended for daily use, is from about 0.1 or 0.15 to about 15 percent by weight of the skin-renewal stimulating-cosmetic composition, for example about 9% preferably about 9% and more preferably in the range of about 1 to about 5%. A concentration that stimulates at least a twenty percent increase in skin renewal and induces an immediate irritation level not exceeding 2.0, according to the tests described herein, is preferred. More potent skin peel compositions intended for occasinonal use, usually with professional dermatological supervision, may have a proportion of skin-renewal stimulating acid of up to about 35% for example 7.5 to 30%, preferable from 7.5% to 30 weight percent preferably from 7.5 to 30 weight percent.

Lower concentrations of a hydrophobic skin-renewal stimulating acid of types such as tretinoin which stimulate cellular receptors, are generally effective. Thus a concentration of such hydrophobic acid of from about 0.005 to about 1.0 percent by weight of the skin-renewal stimulating composition, is preferred with from about 0.01 to 0.1 or 0.5 percent being more preferred.

pH of Composition

Skin-renewal stimulating compositions according to this invention should have substantial acidity and be capable of stimulating a substantially acidic environment when applied to the skin. Consumer use, over-the-counter preparations, intended for daily or twice daily application, should be relatively mild, with a pH of from about 4.5 to about 6.0, or even as mild as 6.2. A preferred pH target is near pH 5, for example from pH 4.8 to 5.2.

Professional-use compositions are more acidic, typically with a pH in the range of from 2.5 to 4.5. Such a professional-use composition, for example a skin peel, is stronger and may have a higher proportion of skin-renewal stimulating acid, for example from 7.5 to 30 weight percent of the composition of a hydrophilic acid, or several percent, up to about five weight percent of the composition of a retinoid.

Preferred cosmetic compositions suitable for frequent topical application to their skin by consumers and formulated according to this invention, with sphingosine, have an acidic pH of from about 2 to about 5.5 and can include, or consist essentially of, cosmetically compatible, odor-free and preferably colorless or white, water or alcohol-soluble, skin-cell-renewal stimulating acids for example, a hydroxybenzoic acid or acids, for example 2-hydroxybenzoic acid or an alpha hydroxy acid, for example lactic acid, or mixtures thereof, dissolved in a cosmetically compatible solvent system.

Incorporation of Anti-irritants

We have also been able to demonstrate, with comparative test data, that the efficacy of a skin exfoliant composition, including the inventive skin-renewal stimulating composition. described herein, can be improved by incorporating significant quantities of one or more antioxidants or anti-inflammatory agents in the composition, or both. Common physiologically acceptable and cosmetically compatible antioxidants are vitamins C and E and the vitamin A precursor, β-carotene. Use of both vitamin C and vitamin E or β-carotene will provide both lipid and aqueous phase antioxidant functions.

One function of antioxidants is anti-irritant, increasing the effective acid strength, or dose, any particular individual can tolerate. Other anti-irritants, anti-inflammatory agents and anti-oxidants can be used, in suitably effective amounts, which can be from about 0.1 to about 20 weight percent of the composition, although lower concentrations than 20%, for example 10 or 5% are generally more suitable.

Another important function of anti-oxidants is to control long-term free-radical damage, the effects of which can simulate aging. Free radicals are generated in skin tissues by skin-renewal stimulating acids and because of their potent chemical activity free radicals may disrupt DNA or interfere with protein synthesis. Lacking control, which anti-oxidants can provide, damage attributable to free radicals can accumulate and may eventually negate or reduce the beneficial effects of skin renewal stimulation.

Some suitable anti-oxidants are selected from the group consisting of vitamin C, β-carotene, vitamin E, or α-tocopherol and its derivatives, (or mixed tocopherols), nordiguaritic acid (NDGA), oat extract, butylated hydroxyanisole (BHA), butylated hydroxytoluene (BHT) ascorbyl palmitate, propyl gallate, rosemary extract, superoxide dismutase, selenium, caffeine, caffeic acid and its derivatives, or mixtures thereof.

BHT, BHA, propyl gallate, NDGA and rosmarinic acid are generally used in rather small proportions, of less than one weight percent, while vitamins C and E, are used in somewhat greater proportions, for example about 1 to 5 weight percent. Some examples of anti-oxidant formulations that can be used with advantage to enhance the skin-renewal stimulating compositions of this invention with approximate percentages by weight of skin-renewal stimulating composition, are:

0.3% BHT, 2% vitamin E, 0.1% vitamin C with 0.1% propyl gallate;

1% oat extract with 2% superoxide dismutase;

5% vitamin C;

0.3% BHT with 0.1% NDGA; and 0.3% BHT with 0.1% rosmarinic acid or rosemary extract.

Some suitable anti-inflammatory agents can be selected from the group consisting of caffeine, theophylline, hydrocortisone, rosemary extract and green tea extract, or mixtures thereof. These agents are preferably used in proportions of about 0.5 to 5.0 weight percent, with the natural extracts being used at the higher end of this range. Some examples of anti-inflammatory formulations that can be used with advantage to enhance the skin-renewal stimulating compositions of this invention, with approximate percentages by weight of skin-renewal stimulating composition, are:

5% rosemary or green tea extract;

0.5 to 2% hydrocortisone;

1.0% caffeine;

0.2% caffeine with 2.0% theophylline;

1.0% alpha-bisabolol; and 5.0% aloe.

A further feature of the invention is the use of materials to control short-term, or immediate irritation, when incorporated in the novel skin-renewal stimulating compositions described herein. Preferably, such anti-irritants comprise from about 0.1 to 20 weight percent, more preferably to 10 weight percent, of the skin-renewal stimulating composition and are selected from the group consisting of antioxidants and anti-inflammatory agents. For example, from about 1 to about 7 percent of rosemary extract, can be included to reduce immediate, or short-term irritation or burning.

Suitable Vehicles

Any cosmetically acceptable vehicles customarily employed for delivering skin-renewal stimulating acids to the skin, hair or nails can be employed in the practice of this invention. Suitable vehicles may be aqueous, or hydroalcoholic, or employ oil or other hydrophobics in dispersions to provide common formulations into creams, lotions, tonics and the like. If desired, the vehicle can simply be plain water, although small quantities of alcohol or other organic solvent may be needed to dissolve or disperse the small quantities of sphingosine required by the present invention.

In a preferred embodiment, the active ingredients can be formulated in a cosmetically acceptable hydroalcoholic vehicle having from about 40 to 75 weight percent of water, preferably 55 to 65 or about 60%, and from about 25 to 55 weight percent, preferably from about 25 to 35 or about 30 percent of an aliphatic alcohol. While a number of lower aliphatic alcohols, both monohydric and polyhydric can be used, ethanol and propanol are the most preferred choices. Many additives and supplemental materials are known to the art as being useful for incorporation in such vehicles, for example, glycerine up to about 5 percent, preferably 1 or 2 percent is useful as a humectant to counteract the drying effect of the alcohol and to improve the feel of the tonic. Stabilizers, fragrances and colorants are examples of other such additives.

Other suitable vehicles include a hydrophobic dispersion of from about 5 to about 60 weight percent of a hydrophobic fluid dispersed in an aqueous medium, and water.

If necessary, pH adjustment to an acceptable range can be effected with from 0.1 to 10 weight percent of an alkaline medium, for example aqueous sodium hydroxide, arginine or triethanolamine (TEA). Since the pH of the skin-renewal stimulating compositions of this invention has an important bearing on their efficacy, the presence of an appropriate buffer may also be desirable. Any such buffer or buffering system, acting in conjunction with the alkaline medium, should of course act to provide an acidic pH within the ranges described above, and preferably to keep the pH at 4.5 or below. The quantity of buffer will depend upon its strength but will usually be from about 0.1 to 10 weight percent, preferably about 1 or 2 percent. Some suitable buffers are TRIS (trimethylolaminomethane) buffers and phosphate buffers.

SKIN-RENEWAL-STIMULATING ACID: EFFICACY TESTING

A simple cell renewal assay was used to determine the effectiveness of various skin-renewal stimulant acid compositions in improving skin condition. The ability to promote cell renewal has been found to be an effective marker indicating, or associated with, what are known as anti-aging benefits including, firming of the skin, increasing skin thickness and reducing the appearance of lines and wrinkles.
PROCEDURES
Determination of Cell-renewal Increase % At least five panelists for each test, and preferably twenty, are patched with 5% dansyl chloride, a fluorescent stain, in petrolatum, on four test sites, two on each volar forearm, or elsewhere, as indicated. The subjects are examined on day 1 to ensure the stain has taken. Using three sites on each panelist and leaving the fourth as a control, test samples are applied with Q-tips, to randomized sites. The panelists are examined at intervals, commencing at day 7, using a quartz mineral light to detect the presence of residual stain at the test sites, examination continuing until the stain is removed.

Additionally, on day 1 and at the end of the study, all test sites, including the controls, are gently scrubbed with a detergent solution to remove loosely adhering squames which are then quantified as cell renewal increase %, using known cell counting techniques.
Determination of Induced Irritation Irritation was evaluated by comparative chromaticity determinations of skin color, by industry standard methods, employing a Minolta Chroma Meter, Minolta Camera Co. Ltd, giving a* readings of skin redness. In general, a* values obtained from the cheeks of volunteers range from about 6 for very pale whitish skin to about 25 on very red skin with a sunburned appearance. Preparatory tests indicated that induction of irritation by application of methyl nicotinate, or balsam of Peru, to the skin of volunteers, increased a, readings by about 5–10 units, reflecting severe irritation. For comparative purposes, an arbitrary scale was devised in which 1.0 irritation unit was equivalent to a difference of 2.5 chromaticity units on the a* scale, as follows:

| Increase in a* | Irritation Index |
|---|---|
| 10.0 | 5.0 |
| 7.5 | 4.0 |
| 5.0 | 3.0 |
| 2.5 | 2.0 |
| 0.0 | 1.0 |

Additional, subjective perceptions of stinging, burning and skin redness after application were recorded, and the data were correlated with the clinical irritation index tabulated above to provide comparative indications of reported and observed irritation. On this scale of from 0 to 5, 0 indicates no discernible or reported irritation, and 5 indicates severe irritation.

EXAMPLE 1

Preparation of a Skin-renewal-Stimulating Cream With Lactic Acid

Phase A:

The following ingredients are combined in the proportions indicated, being weight-for-weight proportions based on the final composition, as are all proportions in these examples:

| Water | 71.15 |
|---|---|
| Propylene Glycol | 5.00 |
| Xanthan | 0.25 |
| Phenoxyethanol | 0.30 |

The xanthan gum is added to water while mixing, and heated to 75° C., when the remaining Phase A ingredients are added.
Phase B:

The following ingredients are heated together, with mixing, until uniform:

| Caprylic or capric triglyceride | 4.00 |
|---|---|
| Stearic Acid | 4.50 |
| Mineral Oil | 6.00 |
| Dimethicone | 1.00 |
| Cetyl Alcohol | 1.50 |
| Cetearyl Alcohol | |
| Ceteareth-20 | 1.50 |
| Glyceryl Stearate | 0.75 |
| PEG-100 Stearate | 0.75 |
| Steareth-2 | 0.20 |
| Sphingosine | 0.10 |

Phase B is added to Phase A and mixed. The mixture is cooled to 40° C., while mixing The following alpha hydroxy carboxylic acid is added with mixing and the mixture is cooled to 25° C.:
Phase C:

| Lactic acid | 3.00 |
|---|---|

The Preparation of adjusted, if necessary to 3.5% to 5.0.

EXAMPLE 2

Preparation of a Skin-renewal-Stimulating Lotion With Lactic Acid

The procedure of Example 1 was repeated using the following ingredients in the weight-for-weight proportions indicated:
PHASE A:

| PHASE A: | Water | 82.65 |
|---|---|---|
| | Propylene Glycol | 5.00 |
| | Xanthan | 0.05 |
| | Phenoxyethanol | 0.30 |
| PHASE B: | Stearic Acid | 1.20 |
| | Mineral Oil | 2.00 |
| | Lanolin Oil | 2.00 |
| | Dimethicone | 0.50 |
| | Cetyl Alcohol | 1.50 |
| | Cetearyl Alcohol with | 0.50 |

|         | Ceteareth-20      |      |
|---------|-------------------|------|
|         | Glyceryl Stearate | 0.50 |
|         | PEG-100 Stearate  | 0.50 |
|         | Steareth-2        | 0.20 |
|         | Sphingosine       | 0.10 |
| PHASE C:| Lactic Acid       | 3.00 |

EXAMPLE 3

Preparation of a Skin-renewal-Stimulating Toner With Lactic Acid

The following ingredients are mixed together until uniform:

| Lactic Acid       | 1.00  |
|-------------------|-------|
| Ethanol SDA 40    | 50.00 |
| Benzyl Alcohol    | 0.10  |
| Sphingosine       | 0.05  |
| PPG-5-Ceteth 20   | 1.00  |
| PPG-3 Myristyl Ether | 0.50 |
| Water             | 47.35 |

The manufacturing approach used in these examples is generally applicable to the formulation of a wide range of cosmetic materials having skin-renewal stimulating properties with long-term control of irritation, according to this invention. In general terms, an appropriate alpha hydroxy or other acid is dissolved in suitable, cosmetically acceptable or compatible solvents and the resultant solution, or solutions, is admixed with conventional cosmetic ingredients, including moisturizers, humectants, stabilizers, fragrances, colorants and the like, as desired by the formulator or customer. Optional ingredients of the invention, such as buffers and anti-irritants, including anti-inflammatories and anti-oxidants, can also be incorporated, as appropriate.

Skin-renewal Stimulation Efficacy of Various Skin Lipids

Four skin lipid materials were examined individually, without other agents present, to determine their abilities, if any, to stimulate skin cell renewal. The lipids comprised bovine brain extracts of research grade material with greater than 90% purity of cerebrosides, ceramides and sphingosine, at the concentrations shown, supplied by Sigma Chemical Co., St. Louis, Mo. The phospholipid employed in these examples was research grade, purified soy lecithin, also from Sigma Chemical Co.

These four materials constituted the examined skin lipids. The examined skin lipids were agitated and dissolved or dispersed in a 1:1 water/ethanol SD 40 solvent vehicle. Where appropriate, the pH was adjusted with 99% TEA (triethanolamine). These solutions or dispersions of skin lipids to be examined were incorporated into cosmetic test samples to provide the desired concentrations.

Test samples, in the following tests, comprise aliquots of skin-renewal stimulating cream compositions (or controls) based on that set forth in Example 1 with variations of proportions, conditions and ingredients, as shown in the test results tabulated below. The data set forth in Table 1 were obtained using the above-described skin lipid materials alone:

TABLE 1

| Material | Concentration | % Increase in Cell Renewal |
|----------|---------------|----------------------------|
| phospholipids | 0.10% | +0.6% |
|          | 1.00%    | +1.4% |
|          | 10.00%   | +7.3% |
| cerebrosides | 0.10% | +4.5% |
|          | 1.00%    | +11.2% |
| ceramides | 0.1%    | +3.7% |
|          | 1.00%    | +6.6% |
| sphingosine | 0.01% | +2.2% |
|          | 0.10%    | +4.9% |
|          | 1.00%    | +7.9% |
| vehicle (control) | 100.00% | +4.5% |

Referring to Table 1, it can be seen that although the examined skin lipid constituents provide a small stimulation or increase of cell renewal the degree is minimal. Looking to the foot of the table, the control vehicle alone provides a base line stimulation of 4.5%. Accordingly, any stimulation below 4.5% is of not of interest for a commercial product having useful activity. The phospholipid, at a concentration of 10%, ceramides at a concentration of 1.0% and sphingosine at a concentration of 1.0% provide an increase of cell renewal in a range of from 6% to 8% slightly above the control value, but not enough to be of significant commercial interest. Cerebrosides at a concentration of 1.0% show a somewhat greater stimulation at 11.2% increase in cell renewal. This figure is still quite modest when compared with an increase of 20–30% which is obtainable with a number of simple, inexpensive acids, including alpha hydroxy acids. Accordingly, these four classes of skin lipids are of little interest for stimulating cell renewal although cerebrosides show somewhat more activity than the other materials. None looks suitable as an alternative to a retinoic or alpha hydroxy skin-renewal stimulant. Note, this was a clinical study performed on human volunteers and is believed to be more indicative of the actual performance of topically applied cosmetic ingredients than are in vitro or animal studies.

Control of Immediate Irritation by the Examined Skin Lipids

The ability of the examined skin lipids to control "immediate" irritation was determined by comparative chromaticity measurements of the skin of volunteers after treatment with balsam of Peru at time zero and after 30 minutes. "Immediate" is used in the sense of an irritation reaction inducing a physiological response that commences immediately upon application of the test sample, although it may take some minutes to peak and become perceptible. The effect is a primary irritation effect that can be contrasted with secondary, long-term irritation that may take weeks to develop. In Table 2, the results from clinical experiments employing 1% concentrations of a phospholipid, cerebrosides, ceramides, and sphingosine show the respective abilities of these substances to control immediate irritation, as compared with water and a known anti-irritant, 5% kola solution.

TABLE 2

| Skin Treatment | a* value time = 0 min. | a* value time = 30 min. |
|----------------|------------------------|--------------------------|
| no treatment   | 6.2 | 6.1 |
| 8% balsam of Peru | 6.1 | 15.2 |
| water only     | 6.0 | 13.9 |
| positive control (5% Kola) | 6.1 | 7.7 |

TABLE 2-continued

| Skin Treatment | a* value time = 0 min. | a* value time = 30 min. |
| --- | --- | --- |
| 1% phospholipids | 6.2 | 14.4 |
| 1% sphingosine | 6.1 | 13.9 |
| 1% ceramides | 6.0 | 14.2 |
| 1% cerebrosides | 6.2 | 14.9 |

Referring to Table 2, at time zero before the irritation due to the balsam of Peru had time to develop, all the test samples had very similar a* readings on the Minolta Chromaticity Meter, indicative of normal skin color. The results at thirty minutes show reddening to a reading of 15.2 for balsam of Peru alone and that water alone reduces this reddening slightly (to 13.9). The positive control, a 5% kola anti-irritant solution exhibited a marked suppression of the irritant effect of balsam of Peru, reducing the thirty-minute reddening to an a* reading of 7.7. None of the examined skin lipids was any better than water in reducing 30-minute reddening.

Clearly, from these data, none of the examined skin lipids is suitable for use as a topical anti-irritant to control immediate or short-term irritation, or more specifically as a short-term suppressant of balsam-of-Peru-induced irritation. To explore the possibly more subtle properties that my theory suggested sphingosine might have, more difficult and elaborate longer term studies were conducted, the results of which are reported in Table 3. Irritation is reported in terms of the index described above, as a differential chromaticity measurement, or Δa*. A base composition comprising 1% lactic acid and 2% 2-hydroxybenzoic acid in a hydroalcoholic toner solution, at a pH of about 3 was used as a skin-renewal stimulating acid composition. A suitable cosmetically acceptable hydroalcoholic vehicle having from about 40 to 75 weight percent of water, preferably 55 to 65 or about 60%, and from about 25 to 55 weight percent, preferably from about 25 to 35 or about 30 percent of an aliphatic alcohol, preferably propanol, or alternatively ethanol, is used. Additives and supplemental materials known to the art as being useful for incorporation in such vehicles, for example, glycerine up to about 5 percent, preferably 1 or 2 percent is useful as a humectant to counteract the drying effect of the alcohol and to improve the feel of the tonic, stabilizers, fragrances and colorants, can also be used.

If necessary, pH adjustment to an acceptable range can be effected with from 0.1 to 10 eight percent of an alkaline medium, for example aqueous sodium hydroxide, arginine or triethanolamine (TEA). A composition of 2-hydroxybenzoic acid and lactic acid is effective in stimulating skin cell renewal while exhibiting low levels of immediate irritation.

Panelists in the following tests, applied test samples to test sites, as described above. At least five panelists were used for each result. For long-term irritation and skin-renewal stimulation determinations, test samples were applied on a twice daily basis, morning and night. The test samples comprised aliquots of skin-conditioning cream compositions equivalent to the composition set forth in Example 1 hereinabove, with the omission of sphingosine (except as indicated below) and the addition of the respective test ingredients, as appropriate. Tretinoin (retinoic acid) was used in a commercially available cosmetic formulation in a concentration of about 0.05%.

TABLE 3

| Composition | Irritation Induced Immediate | Irritation Induced After 4 Weeks Use | Cell Renewal % Incr. |
| --- | --- | --- | --- |
| Base composition (alone) | 2.6 | 2.2 | 22 |
| Base with the indicated additional ingredient: | | | |
| 0.1% phospholipids | 2.5 | 2.0 | 20 |
| 1.0% phospholipids | 3.0 | 2.2 | 25 |
| 0.1% cerebrosides | 2.4 | 2.1 | 21 |
| 1.0% cerebrosides | 2.3 | 2.1 | 19 |
| 0.1% ceramides | 2.4 | 2.3 | 18 |
| 1.0% ceramides | 2.3 | 2.2 | 22 |
| 0.1% sphingosine | 2.3 | 1.5 | 23 |
| 1.0% sphingosine | 2.4 | 1.8 | 18 |
| 0.01% sphingosine | 2.3 | 1.6 | 21 |
| positive control 5% kola nut extract | 1.4 | 1.7 | 20 |
| tretinoin alone | 1.7 | 3.1 | 33 |
| tretinoin with 0.1% sphingosine | 1.8 | 2.2 | 34 |

Table 3 shows the effect of the four classes of examined skin lipids, at different concentrations, upon irritation levels induced by the base composition of skin-renewal stimulating hydroxy acids, after four weeks of continuous daily use. Their efficacy as skin-renewal stimulants is also reported. To understand whether the test material exerts any long-term control of irritation, the four week reading has to be compared with the immediate reading. Any significant reduction, at four weeks, is suggestive that the test material is effective in controlling long-term irritation. For any apparent activity to be significant, the degree of suppression of irritation should reduce the irritation index below the figure for the base composition alone. The first line of data in Table 3 shows that the unsupplemented base composition exhibits a decline, from an irritation index value of 2.6, induced immediately (30 minutes) after application of the base hydroxy acid skin-renewal promotion composition, to 2.2 after four weeks of use.

Seen in this light, only sphingosine, at all concentrations, shows a significant reduction of long-term irritation with a decline, for the 0.1% sample of more than 30%.of the scale value, from 2.3 to 1.5. The other examined skin lipids show little, if any reduction. The results for a 1% concentration of phospholipids are anomalous in that the immediate reported effect of the phospholipid in this test was to increase the irritation level. The resultant decline at four weeks was to a figure substantially the same as that for the base used alone. Clearly, the tested phospholipid is of no interest in controlling long-term irritation induced by the base hydroxy acid composition.

When used with the 2-hydroxybenzoic acid-lactic acid skin-renewal stimulant base described above, sphingosine exerted a pronounced long-term irritation-controlling effect which, surprisingly, was not exhibited by the other classes of examined biologically active skin lipids namely the phospholipids, cerebrosides and ceramides. Reference to the cell renewal percentage increases reported for various combinations of the cell-renewal stimulant acid, or acids, and examined skin lipids shows that, in general, the presence of the examined skin lipid materials had little depressant effect upon the cell-renewal stimulatory activity of the base composition. A concentration of 0.1% sphingosine was particularly interesting, showing the lowest irritation level at four weeks of any material tested. That concentration of sphingosine also exhibited the best cell-renewal percentage increase of the sphingosine samples and at 23% this was one of the higher results for samples employing a 2-hydroxybenzoic acid-lactic acid base.

The positive control, a 5% kola anti-irritant solution had an immediate effect of substantially suppressing irritation but, in spite of the continued presence of kola in the test composition, by four weeks the irritation level had risen substantially, from 1.4 to 1.7, indicating a long-term irritation phenomenon not subject to control by topically applied kola.

Kola nut or rosemary extract and other anti-irritants are of course optional ingredients for inclusion in the novel compositions of this invention. Combined with sphingosine, such anti-irritants can be expected to produce good control of both immediate irritation and long-term irritation, and the four-week values may even be improved over those shown in Table 3, by such a combination. Because sphingosine is a subtle biochemical agent capable of mediating cellular activity, we believe that the benefits brought to skin-renewal stimulating compositions by the presence of sphingosine, according to the teachings of the present invention, may be more pronounced with periods of use longer than the four weeks that was practical for the above tests. Normal use is for eight to twelve weeks, which may then be followed by maintenance usage for indefinite periods. Accumulative small benefits become more significant over extended periods of use, especially with large populations of users. Also, sphingosine may bring subtle advantages of skin conditioning that are only manifested with extended use.

A concentration of 0.1% sphingosine has a dramatic effect when used in combination with tretinoin, as revealed by this test regimen. Referring to the next to last line of Table 3, the long-term irritation capability of tretinoin is clearly shown as rising to 3.1 after four weeks from a modest initial value of 1.7 when tretinoin is used alone. When 0.1% sphingosine is added to tretinoin (last line of Table 3), tretinoin's severe four-week irritation is substantially reduced from 3.1 to 2.2. The high skin cell-renewal stimulant activity of tretinoin was not diminished.

In summary, the comparative data of Table 3 shows that sphingosine alone of the examined skin lipids displays a distinct ability to control four-week irritation induced by multiple classes of skin-renewal stimulant acids without significantly diminishing their activity.

The effect of sphingosine on individual alpha hydroxy carboxylic acids was determined by conducting cell renewal and four week irritation tests as described above. The following results were obtained.

TABLE 4

| Composition | % Increase in Cell Renewal | Irritation Induced | Efficacy Safety Factor |
| --- | --- | --- | --- |
| 2% lactic acid pH 3 | 22 | 2.6 | 8.46 |
| + 0.01.% sphingosine | 23 | 1.9 | 12.10 |
| + 0.10% sphingosine | 26 | 1.6 | 16.25 |
| 2% lactic acid pH 6 | 16 | 1.9 | 8.42 |
| + 0.10% sphingosine | 24 | 1.4 | 17.14 |
| 5% lactic acid pH 6 | 29 | 3.5 | 8.29 |
| + 0.10% sphingosine | 30 | 2.2 | 13.63 |
| 1% 2-hydroxybenzoic acid pH 3 | 22 | 2.5 | 8.80 |
| + 0.10% sphingosine | 24 | 1.9 | 12.63 |
| 1% 2-hydroxybenzoic acid pH 6 | 17 | 2.2 | 7.7 |
| + 0.10% sphingosine | 26 | 2.0 | 13.0 |

The efficacy safety factor used in this table weights the cell-renewal stimulating activity of the hydroxy acid against the irritation induced by dividing the cell renewal % increase by the irritation level. Referring to the data in this table, it can be seen that sphingosine has a modest ability to stimulate the cell renewal increasing capability of simple alpha hydroxy acids, such as lactic acid and 2-hydroxybenzoic acid. The preferred concentration of 0.1% sphingosine was effective in raising the cell renewal percentage increase by three points for a 2% lactic acid solution at the more strongly irritating pH of 3, and by eight points at pH 6 with comparable numbers being shown for 2-hydroxybenzoic acid. There is little improvement of cell renewal stimulation when a higher concentration of about 5% of lactic acid is used. Here, the cell renewal efficiency is probably close to a maximum, at 29%, and is hard to improve. The overall impact of sphingosine on the suitability of hydroxy acids such as lactic acid and 2-hydroxybenzoic acid for skin-renewal stimulation with controlled long-term irritation, is clearly demonstrated by comparing the higher values of the efficacy safety factor obtained when sphingosine is present with the lower values obtained when it is not.

In general, cosmetic formulations with a pH of the order of 6 are suitable for over-the-counter consumer sales for daily use, while those with a lower pH of 3 are more suitable for use under professional supervision by physicians or licensed beauticians.

The potential wider applicability of the invention to controlling, or compensating for, undesired side effects of cell-proliferation stimulating agents, at large, is suggested by the following data in Test 5. To obtain the reported results, subjects on aggressive alpha hydroxy acid therapy for clinical skin disorders were evaluated for sphingosine content in their skin. The surface of the skin of test subjects was swabbed several times with methanol to extract methanol-soluble skin-lipid components. The extracts were pooled, dried and resuspended in 100 μl. 1:1 chloroform/methanol and examined by high performance thin-layer chromatography. Calibration against standards for sphingosine, ceramides and cerebrosides, using densitometry, enabled changes in sphingosine to be quantified. Determinations were made on subjects before treatment, after four weeks and after eight weeks. The results are shown in Table 5.

TABLE 5

| Skin lipid component | % change after | |
| --- | --- | --- |
| | four weeks | eight weeks |
| ceramides | n.s. | n.s. |
| cerebrosides | n.s. | −8% |
| sphingosine | −11% | −37% |

"n.s." is "not significant".

These findings show a clear and selective decline in sphingosine levels accompanying alpha hydroxy acid treatment. This decline is not shared by the other skin lipid components tested, there being no apparent decline of ceramides and only a minor decline of cerebrosides. This data leads to the conclusion that a decline in sphingosine may be an important side-effect of the altered skin metabolism wrought by cell-renewal stimulating acids such as alpha hydroxy acids.

While this invention is not limited by any particular theory, we have developed a theory, not taught by any prior art known to us, that relates our discoveries regarding sphingosine to concepts of cell proliferation and differentiation. In accordance with our theory, it appears that a high degree of cell renewal stimulation may reduce or hinder differentiation. Thus the peeling brought about as an early effect of strong skin acid compositions is a desquamation of immature cells resulting from over-stimulation of cell renewal. In time, the stimulus is less and more mature cells are generated.

Cerebrosides, ceramides and sphingosine are known to be substantially interconvertible in skin tissues. Cerebrosides lose a sugar to become ceramides. Cleavage of a fatty acyl chain from ceramides yields sphingosine. Sphingosine is synthesized in basal keratinocytes in inner layers of the skin. It is also known that maturation of the epidermis, proceeding outwardly to the skin surface, is accompanied by a decrease in content of cerebrosides while ceramides increase. Ceramides are a potential exogenous source of sphingosine, by de-acylation, as described above.

With this background, we have speculated that if cells are stimulated to grow faster than normal, they have too little time to produce adequate sphingosine. It has occurred to us that ceramide breakdown rates, as the cells mature into stratum corneal cells, may be inadequate. Or synthesis of sphingosine in basal keratinocytes may be inadequate. This speculation is verified by, and represents an interpretation of, the findings reported in Table 5. Noting the importance of sphingosine-based ceramides to the barrier function of epithelial tissues, the data of Tables 1–4, when seen in the light of this hypothesis, suggest this invention may have a wide applicability to controlling side effects of cell proliferation stimulants by applying or administering sphingosine along with such stimulants.

Besides the skin-renewal stimulating acids described herein, other agents such as drugs ad hormones are capable of stimulating epithelial cell proliferation, for example retinoid drugs, vitamin $D_3$ also known as cholecalciferol, epithelially active growth hormones, for example somatotropin also known as human growth hormone, epidermal growth factor and various glandular extracts. Pursuant to the foregoing insights, the present invention includes uses of sphingosine that are effective to control side effects of such other agents.

Thus, in this aspect, the invention provides a cell-renewal stimulating composition for topical application to epithelial tissue comprising sufficient of an active, cell-renewal stimulating agent to stimulate increased cell proliferation, which agent can induce deferred hyperproliferative allergenicity and is formulated together with a proportion of sphingosine material sufficient to compensate for sphingosine deficiencies attributable to cellular immaturity.

Preferably, the cell-renewal stimulating agent is selected from the group consisting of hydrophilic, skin-cell-renewal stimulating acids, hydrophobic skin-cell-renewal stimulating hydrophobic acids, cell-proliferation stimulating hormones and cell-proliferation stimulating drugs. However less specifically active products, for example moisturizing cosmetics, which though not incorporating a skin-cell-renewal stimulating acid, nevertheless display a delayed irritation attributable to skin cell hyperproliferation, can be improved by incorporating a sphingosine material, in the manner described herein, to control delayed or long term irritation.

Preferably, the inventive cell-renewal stimulating composition is for topical application to normal skin on a frequent basis, and has an acidic pH, wherein the cell-renewal stimulant agent is a skin-cell renewal stimulant acid or acids present at a sufficient concentration to improve the appearance of the skin, the sphingosine being present at a sufficient concentration to control long-term irritation.

Application Rates and Frequencies

Typical application rates of the inventive skin-renewal stimulating compositions described herein can range from about 0.01 to 0.5 mg of active acid ingredients per square centimeter of skin, where the acid is a low-molecular weight hydrophilic acid, such as an alpha hydroxy carboxylic acid, with a range of from 0.05 to 0.2 mg/cm$^2$ being preferred. Cosmetic creams are generally applied at a rate of about 2–3 mg/cm$^2$. With an active ingredient proportion of about 0.15 to about 30 weight percent, this gives a possible rate of application of active ingredients of from about 0.003 mg/cm$^2$ to 0.9 mg/cm$^2$. A preferred range is from about 0.01 to 0.5 mg/cm$^2$, with a range of from 0.05 to 0.2 mg/cm$^2$ active ingredient per unit skin area being more preferred. Using a preferred proportion of about 3% active acidic ingredients, in total, gives a preferred application rate of 0.06 to 0.09 mg/cm$^2$.

Hydrophobic skin-renewal stimulating acids, such as retinoic acids are usually used in substantially lower concentrations, for example from 20 to 200 times less concentrated.

This dosage is applied to whatever skin area requires treatment, preferably twice a day. More frequent applications of three or four times a day are likely to be wasteful of product without providing additional benefits, whereas less frequent applications, notably once a day, result in reduced efficacy. Additional applications may occasionally be made after washing, bathing or swimming, up to a maximum of about six times a day.

The inventive use of sphingosine in skin-renewal stimulant compositions is of particular value in controlling long-term irritation in daily or repeated use cosmetic formulations. The formulations described herein are generally lower strength non-prescription or consumer preparations although advantages may also be obtained using sphingosine in higher-strength professional preparations intended for use under the supervision of dermatological professionals. Such higher strength preparations will be more acidic, with a pH below about 4.0, for example in the range of from 2.0 to 3.5. They will also have a higher concentration of acidic ingredient or ingredients, with sphingosine incorporated in a proportionately higher concentration. Such higher concentration can be in the range of about 10 to 30 weight percent of the composition of hydrophobic skin-renewal stimulant acid. For a hydrophobic, cell-membrane receptor-active, skin-renewal stimulant, such as a retinoic acid, a higher concentration of about 0.1 to 1.0 weight percent can be used. Such high-strength compositions generally are skin peels, acting to cause skin to peel after only one or two treatments. High strength compositions are generally not suitable for frequent, repeated application.

Long-term irritation, control of which is a benefit provided by sphingosine, is compounded by frequent applications of a skin-renewal stimulant acid. Many daily use cosmetic preparations on the market now include a skin-renewal stimulating acid that may produce such long-term irritation. Indeed, conventional moisturizer formulations, lacking skin-renewal stimulating acids, can also induce hyperproliferation of skin cells. Inclusion of sphingosine as well as a short-term or immediate anti-irritant and an anti-oxidant, in accordance with the teachings of the invention herein, can alleviate these problems.

The consumer preparation is used on any desired skin area, including the face, while the professional preparation can be applied to spot defects. The consumer composition can be helpful in alleviating problems of wrinkles, sun damage and cracking with some effect on age spots, while the professional composition can be more effective on age spots, keratoses and other more serious skin problems.

One preferred regimen comprises a regular program of twice daily treatments for an indefinite period employing a consumer-use formulation preferably having the more preferred ingredients and proportions of the invention, as set forth above. Such preferred compositions desirably have a proportion of active hydrophilic acid ingredients of about 2–7% and a pH in the range of about 4.5 to 6.0, preferably, close to 5. Such a continual regimen is preferably accompanied by dermatological clinic visits to monitor progress. While a high initial dose to obtain prompt improvement could be used, such may elicit a high initial irritation rate. These above-described dosages are generally appropriate for the application of a skin-renewal stimulating cream to most exposed or exposable skin surfaces, but such would generally not be appropriate for application to the scalp.

An alternative regimen comprises a twice daily treatment for about 8 to 12 weeks followed by maintenance applications of the the inventive composition on a daily basis, or about three times per week.

While an illustrative embodiment of the invention has been described above, various modifications will be apparent to those of ordinary skill in the art. Such modifications are within the spirit and scope of the invention, which is limited and defined only by the appended claims.

I claim:

1. A method of controlling long-term irritation induced by at least daily application of a composition comprising a skin cell renewal acid after at least about four weeks topical application of said composition wherein said skin cell renewal acid comprises an acid selected from the group consisting of retinoic acid, hydroxy benzoic acid and an alpha hydroxy acid selected from the group consisting of glycolic acid, lactic acid, malic acid, tartaric acid, citric acid and ascorbic acid, and wherein said composition has a pH of 2.5 to 6.2, the method comprising adding to the composition 0.001 to 5 percent of sphingosine to provide a sphingosine-containing composition and at least daily topical application of the sphingosine-containing composition.

2. A method of controlling long-term irritation induced by at least daily application of a composition comprising a skin cell renewal acid after at least about four weeks topical application of said composition wherein said skin cell renewal acid comprises an acid selected from the group consisting of a retinoid, a hydroxy benzoic acid and an alpha hydroxy acid, and wherein said composition has a pH of 2.5 to 6.2, the method comprising adding to the composition 0.001 to 5 percent of a sphingosine compound selected from the group consisting of, sphingosine, phytosphinganine, dihydrosphingosine, enantiomers and mixtures of the foregoing, and comprising at least daily topical application of the resultant sphingosine-supplemented composition.

3. A method according to claim 1 wherein said long-term irritation controlled by said sphingosine material is redness irritation induced by said acid and shown to be reduced by comparative chromaticity determinations.

4. A method according to claim 1 further comprising adding from about 0.1 to 20 weight percent of an anti-irritant selected from the group consisting of antioxidants and anti-inflammatory agents to the cosmetic composition.

* * * * *

UNITED STATES PATENT AND TRADEMARK OFFICE
CERTIFICATE OF CORRECTION

Page 1 of 2

PATENT NO. : 5,616,332
DATED : April 1, 1997
INVENTOR(S) : Morris Herstein

It is certified that error appears in the above-indentified patent and that said Letters Patent is hereby corrected as shown below:

On the title page, please insert the following references (set forth in Applicant's PTO 1449 filed with patent application no. 08/097,380 on July 23, 1993) as follows:

| | | |
|---|---|---|
| 5,149,860 | dated SEptember 22, 1992 | ZYSMAN et al. |
| 4,952,683 | dated August 28, 1990 | TSCHANNEN et al. |
| 5,110,987 | dated May 5, 1992 | LIOTTA et al. |
| 4,937,328 | dated June 26, 1990 | SCHMIDT et al. |

OTHER DOCUMENTS

The Merck Index Eleventh Edition 1989 Monograph #8703
Mirabella January 1993 pp 60-61
Gupta et al. "Sphingosine Inhibits Phorbol Ester-Induced ...etc." The J. of Investigative Dermatology 91, pp 486-491 (November '88)
Rieger et al. "Skin Constituents as Cosmetic Ingredients" Cosmetics and Toiletries v. 107 pp 85-94 (November '92)

"The World of Ceramides" Elizabeth Arden Co. Advertisement '93

Petersen "Ceramides" Cosmetics and Toiletries v. 107 pp 45-49

UNITED STATES PATENT AND TRADEMARK OFFICE
CERTIFICATE OF CORRECTION

PATENT NO. : 5,616,332
DATED : April 1, 1997
INVENTOR(S) : Morris Herstein

It is certified that error appears in the above-identified patent and that said Letters Patent is hereby corrected as shown below:

Jass et al. "The Living Stratum Corneum" *Cosmetics and Toiletries* v. 106 pp 47-53 (OCtober '91)

Signed and Sealed this

Second Day of June, 1998

Attest:

BRUCE LEHMAN

*Attesting Officer*    Commissioner of Patents and Trademarks